United States Patent [19]

Frickel et al.

[11] Patent Number: 4,760,174

[45] Date of Patent: Jul. 26, 1988

[54] TETRALIN DERIVATIVES, THEIR PREPARATION AND THEIR USE

[75] Inventors: Fritz-Frieder Frickel, Deidesheim; Hans-Heiner Wuest, Dossenheim; Axel Nuerrenbach, Gruenstadt, all of Fed. Rep. of Germany

[73] Assignee: BASF Aktiengesellschaft, Fed. Rep. of Germany

[21] Appl. No.: 778,190

[22] Filed: Sep. 20, 1985

[30] Foreign Application Priority Data

Sep. 22, 1984 [DE] Fed. Rep. of Germany ....... 3434942

[51] Int. Cl.[4] .................... C07C 59/76; C07C 19/76
[52] U.S. Cl. ............................... 562/462; 514/150;
514/381; 514/385; 514/396; 514/529; 514/545;
514/569; 514/682; 534/552; 534/564; 548/235;
548/261; 548/335; 548/341; 549/31; 558/414;
558/423; 560/51; 560/56; 560/139; 585/400;
564/169; 564/172; 564/176; 564/177; 568/328;
568/632; 568/735; 568/736
[58] Field of Search ............... 562/462; 514/100, 381,
514/385, 396, 529, 545, 569, 682; 534/152, 564;
548/235, 261, 335, 341; 549/31; 558/414, 423;
560/51, 56, 139

[56] References Cited

FOREIGN PATENT DOCUMENTS 2854354 7/1978 Fed. Rep. of Germany .
3202118 7/1983 Fed. Rep. of Germany .

Primary Examiner—Paul J. Killos
Attorney, Agent, or Firm—Keil & Weinkauf

[57] ABSTRACT

Tetralin derivatives of the formula I

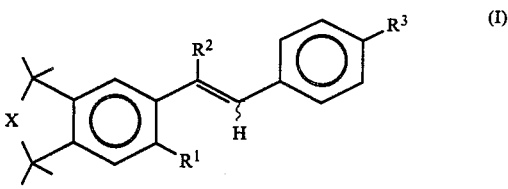

where X, $R^1$, $R^2$ and $R^3$ have the meanings stated in the description, and their preparation are described. The novel compounds are useful for the treatment of disorders.

17 Claims, No Drawings

TETRALIN DERIVATIVES, THEIR PREPARATION AND THEIR USE

The present invention relates to novel tetralin derivatives, their preparation and their use for the treatment of disorders.

It has been disclosed, for example in German Laid-Open application DOS No. 2,854,354 and DOS No. 3,202,118, that vinylbenzoic acid derivatives have pharmacological effects in the topical and systemic therapy of neoplasias, acne, psoriasis and other dermatological affections. However, these vinylbenzoic acid derivatives are not always satisfactory.

We have found that tetralin derivatives of the formula I

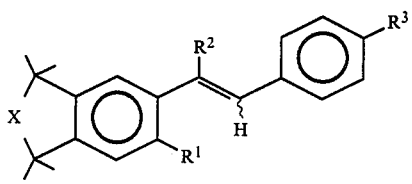

where $R^1$ is hydrogen, $C_1$–$C_4$-alkyl, $C_1$–$C_4$-alkoxy or halogen, $R^2$ is hydrogen, $C_1$–$C_6$-alkyl or $C_3$–$C_6$-cycloalkyl, X is —CH$_2$—CO—, —CH$_2$—CHOH—, —CH$_2$—C(R$^4$)OH—, —CH$_2$—C(OCOR$^4$)H—, —CH$_2$—C(R$^4$)(OCHOR$^5$)—, —CHOH—CHOH—, —CH=CH—, —CH(OCOR$^4$)—CH(OCOR$^4$)—, —CH$_2$—CH(OR$^4$)— or

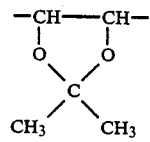

(where $R^4$ and $R^5$ are each $C_1$–$C_4$-alkyl and $R^3$ is nitrile, $C_2$–$C_{10}$-ketal or ∫CH(R$^7$)(R$^8$)— or —CO—R$^9$, where $R^7$ is hydrogen or $C_1$–$C_3$-alkyl, $R^8$ is hydrogen, $C_1$–$C_3$-alkyl or —OR$^{10}$ or —NR$^{11}$R$^{12}$ (where $R^{10}$, $R^{11}$ and $R^{12}$ are each hydrogen, $C_1$–$C_4$-alkyl, $C_2$–$C_{20}$-alkanoyl or unsubstituted or substituted benzoyl, or $R^{11}$ and $R^{12}$, together with the nitrogen atom to which they are bonded, form a heterocyclic radical) and $R^9$ is hydrogen, halogen, $C_1$–$C_4$-alkyl, azido, imidazolyl, triazolyl or —OR$^{13}$ or —NR$^{14}$R$^{15}$ (where $R^{13}$ is hydrogen or $C_1$–$C_8$-alkyl or is $C_2$–$C_6$-alkyl which is substituted by one or more hydroxyl groups or a $C_1$–$C_4$-alkoxy group, or is unsubstituted or substituted aryl or aralkyl which is unsubstituted or substituted in the aryl moiety, and $R^{14}$ and $R^{15}$ are each hydrogen or $C_1$–$C_6$-alkyl or are each $C_2$–$C_6$-alkyl which is substituted by one or more hydroxyl groups or are each aryl or tetrazolyl, or $R^{14}$ and $R^{15}$, together with the nitrogen atom to which they are bonded, form a heterocyclic ring system possessing 3 to 6 ring atoms) and, where relevant, their physiologically tolerated salts have a better action spectrum.

Preferred compounds are the all-E compounds and from among these in particular those compounds in which X is —CH$_2$—CO—, —CH$_2$—CHOH—, —CHOH—CHOH—, or —CH=CH—, $R^1$ is hydrogen, methyl, methoxy or fluorine, $R^2$ is hydrogen or methyl and $R^3$ is —COOH, —COO—$C_1$–$C_4$-alkyl, —CHO, —CH$_2$OH or —CH$_2$—O—CO—CH$_3$.

Typical examples of compounds according to the invention are the following tetralin compounds, which are further substituted in the para-position of the phenyl ring by the radicals listed below ($R^3$ in the general formula I).

1,2,3,4-Tetrahydro-1,1,4,4-tetramethyl-3-oxo-6-(1-methyl-2-phenylethenyl)-naphthalene
1,2,3,4-Tetrahydro-1,1,4,4-tetramethyl-2-oxo-6-(1-methyl-2-phenylethenyl)-naphthalene
1,2,3,4-Tetrahydro-1,1,4,4-tetramethyl-3-hydroxy-3-methyl-6-(1-methyl-2-phenylethenyl)-naphthalene
1,2,3,4-Tetrahydro-1,1,4,4-tetramethyl-3-hydroxy-3-ethyl-6-(1-methyl-2-phenylethenyl)-naphthalene
1,2,3,4-Tetrahydro-1,1,4,4-tetramethyl-3-hydroxy-3-propyl-6-(1-methyl-2-phenylethenyl)-naphthalene
1,2,3,4-Tetrahydro-1,1,4,4-tetramethyl-3-hydroxy-3-butyl-6-(1-methyl-2-phenylethenyl)-naphthalene
1,2,3,4-Tetrahydro-1,1,4,4-tetramethyl-2-methoxy-6-(1-methyl-2-phenylethyl)-naphthalene
1,2,3,4-Tetrahydro-1,1,4,4-tetramethyl-3-methoxy-6-(1-methyl-2-phenylethenyl)-naphthalene
1,2,3,4-Tetrahydro-1,1,4,4-tetramethyl-2-ethoxy-6-(1-methyl-2-phenylethenyl)-naphthalene
1,2,3,4-Tetrahydro-1,1,4,4-tetramethyl-3-ethoxy-6-(1-methyl-2-phenylethenyl)-naphthalene
1,2,3,4-Tetrahydro-1,1,4,4-tetramethyl-3-propoxy-6-(1-methyl-2-phenylethenyl)-naphthalene
1,2,3,4-Tetrahydro-1,1,4,4-tetramethyl-2-propoxy-6-(1-methyl-2-phenylethenyl)-naphthalene
1,2,3,4-Tetrahydro-1,1,4,4-tetramethyl-2-butoxy-6-(1-methyl-2-phenylethenyl)-naphthalene
1,2,3,4-Tetrahydro-1,1,4,4-tetramethyl-3-butoxy-6-(1-methyl-2-phenylethenyl)-naphthalene
1,2,3,4-Tetrahydro-1,1,4,4-tetramethyl-2-acetoxy-6-(1-methyl-2-phenylethenyl)-naphthalene
1,2,3,4-Tetrahydro-1,1,4,4-tetramethyl-3-acetoxy-6-(1-methyl-2-phenylethenyl)-naphthalene
1,2,3,4-Tetrahydro-1,1,4,4-tetramethyl-2-propanoyloxy-6-(1-methyl-2-phenylethenyl)-naphthalene
1,2,3,4-Tetrahydro-1,1,4,4-tetramethyl-3-propanoyloxy-6-(1-methyl-2-phenylethenyl)-naphthalene
1,2,3,4-Tetrahydro-1,1,4,4-tetramethyl-2-butanoyloxy-6-(1-methyl-2-phenylethenyl)-naphthalene
1,2,3,4-Tetrahydro-1,1,4,4-tetramethyl-3-butanoyloxy-6-(1-methyl-2-phenylethenyl)-naphthalene
1,2,3,4-Tetrahydro-1,1,4,4-tetramethyl-2-pentamoyloxy-6-(1-methyl-2-phenylethenyl)-naphthalene
1,2,3,4-Tetrahydro-1,1,4,4-tetramethyl-3-pentanoyloxy-6-(1-methyl-2-phenylethenyl)-naphthalene
1,2,3,4-Tetrahydro-1,1,4,4-tetramethyl-2-hydroxy-6-(1-methyl-2-phenylethenyl)-napthalene
1,2,3,4-Tetrahydro-1,1,4,4-tetramethyl-3-hydroxy-6-(1-methyl-2-phenylethenyl)-naphthalene
1,2,3,4-Tetrahydro-1,1,4,4-tetramethyl-2,3-dihydroxy-6-(1-methyl-2-phenylethenyl)-naphthalene
1,2,3,4-Tetrahydro-1,1,4,4-tetramethyl-2-hydroxy-2-methyl-1(1-methyl-2-phenylethenyl)-naphthalene
1,2,3,4-Tetrahydro-1,1,4,4-tetramethyl-2-hydroxy-2-ethyl-6(1-methyl-2-phenylethenyl)-naphthalene
1,2,3,4-Tetrahydro-1,1,4,4-tetramethyl-2-hydroxy-2-propyl-6-(1-methyl-2-phenylethenyl)-naphthalene
1,2,3,4-Tetrahydro-1,1,4,4-tetramethyl-2-hydroxy-2-butyl-6-(1-methyl-2-phenylethenyl)-naphthalene 1,2,3,4-Tetrahydro-1,1,4,4-tetramethyl-3-hydroxy-3-methyl-6-(1-methyl-2-phenylethenyl) -naphthalene 1,2,3,4-Tetrahydro-1,1,4,4-tetramethyl-2,3-diacetoxy-6-(1methyl-2phenylethenyl)-naphthalene 1,2,3,4-Tetrahydro-1,1,4,4-tetramethyl-2,3-dipropanoyloxy-6-(1-methyl-2-phenylethenyl)-naphthalene 2,2,4,4,9,9-Hexamethyl-6-(1-methyl-2-phenylethyl)-3a,4,9,9,a-tetrahydronaphtho[2,3d]-1,3-dioxole 1,4-Dihydro-1,1,4,4-tetramethyl-6-(1-methyl-2-phenylethenyl)-naphthalene In the above compounds, $R^2$ is methyl. In other compounds according to the invention, $R^2$ is hydrogen, ethyl, propyl, cyclopropyl, butyl, 3-methylpropyl, pentyl or hexyl.

These compounds are further substituted in the para-position of the phenyl ring by the following typical radicals ($R^3$ in the general formula I): carboxyl, methoxycarbonyl, ethoxycarbonyl, propoxycarbonyl, 1-methylethoxycarbonyl, butoxycarbonyl, octyloxycarbonyl, 2-methoxyethoxycarbonyl, 2-hydroxyethoxycarbonyl, 2,3-dihydroxypropoxycarbonyl, benzyloxycarbonyl, cyano, formyl, hydroxymethyl, methyl, ethyl, propyl, chloroformyl, fluoroformyl, azidoformyl, methoxymethyl, ethoxymethyl, propoxymethyl, butyloxymethyl, benzyloxymethyl, acetoxymethyl, propionyloxymethyl, hexadecanoyloxymethyl, aminomethyl, benzoyloxymethyl, 3,4-dimethoxybenzoyloxymethyl, methylaminomethyl, ethylaminomethyl, butylaminomethyl, propylaminomethyl, acetyl, benzoylaminomethyl, 4-methoxybenzoylaminomethyl, acetylaminomethyl, propionylaminomethyl, palmitoylaminomethyl, carbamyl, N-methylcarbamyl, N-(2,3-dihydroxypropyl)-carbamyl, N-ethylcarbamyl, N-hexylcarbamyl, N,N'-dimethylcarbamyl, morpholinocarbamyl, 3-(N-imidazolyl)-carbonyl and 3-(N-triazolyl)-carbonyl.

The novel compounds can be prepared by subjecting a carbonyl compound of the formula (II)

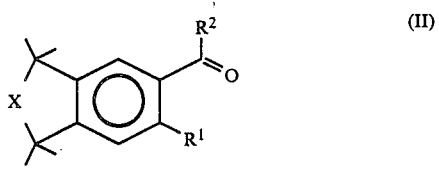

where X, $R^1$ and $R^2$ have the above meanings, to a Wittig-Horner reaction with a phosphorus compound of the formula (III)

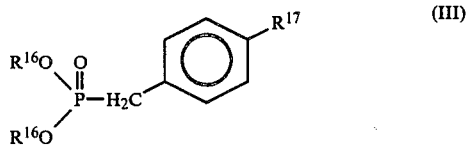

where $R^{16}$ is $C_1$-$C_3$-alkyl and $R^{17}$ is $C_1$- or $C_2$-alkyl, carbo-$C_1$-$C_8$-alkoxy or $C_1$-$C_4$-alkoxymethyl.

The Wittig-Horner reaction is carried out at not higher than 100° C., advantageously at from 20° to 50° C., under atmospheric pressure or in a closed vessel under super-atmospheric pressure, if necessary with heating to the stated temperature.

This reaction can be carried out in the presence of a diluent or solvent, for example a lower saturated dialkyl ether, dialkylglycol ether or cyclic ether, such as diethyl ether, ethyl tert.-butyl ether, 1,2-dimethoxyethane, tetrahydrofuran or dioxane, an aromatic hydrocarbon, such as benzene, or an alkylbenzene, such as toluene or xylene, a saturated aliphatic hydrocarbon, such as hexane, heptane or isooctane, a lower aliphatic ketone, such as acetone, methyl ethyl ketone or methyl isobutyl ketone, a dialkylformamide, such as dimethylformamide or diethylformamide, or a mixture of the stated solvents. Cyclic ethers, such as dioxane or tetrahydrofuran, and in particular dimethylformamide and mixtures of these are preferably used, the reaction taking place in general at up to 30° C.

The reactions are effected in the presence of a deprotonating agent for the phosphate (III), suitable compounds being alkali metal hydrides and alkali metal amides, in particular those of sodium and potassium, the sodium and potassium salts of dimethyl sulfoxide, alkyllithium compounds, such as n-butyl-lithium, or alkali metal alcoholates, preferably sodium methylate and sodium ethylate.

The esters of the formula (I) in which $R^3$ is carboalkoxy are, if desired, converted to the free carboxylic acids by hydrolysis of the ester. Conversely, the free acid can of course be esterified in a conventional manner.

The hydrolysis is carried out in a conventional manner at in general as high as 120° C., preferably at room temperature.

It can be carried out under atmospheric pressure or in a closed vessel under superatmospheric pressure.

Advantageously, the hydrolysis/esterification is effected in the presence of a solvent or diluent, for example a dialkylglycol ether or cyclic ether, such as 1,2-dimethoxyethane, tetrahydrofuran or dioxane, a lower aliphatic ketone, such as acetone, methyl ethyl ketone or methyl isobutyl ketone, and the esterification in particular is carried out in the alcohol provided for the esterification, such as methanol, ethanol, propanol or isopropanol, in the presence or absence of water or in a mixture of the stated solvents with water.

Preferred solvents are aqueous mixtures of ethanol and methanol, the reaction being carried out at the boiling point of the reaction mixture.

The hydrolysis is preferably effected in the presence of an alkali, such as an alkali metal hydroxide, carbonate or bicarbonate, in particular of sodium or of potassium, a tertiary organic base, such as pyridine, or a lower trialkylamine, e.g. trimethylamine or triethylamine, as a mixture with water. The base is used in the stoichiometric amount or in slight excess, based on the ester. Sodium hydroxide or potassium hydroxide is preferably used.

The esterification is advantageously carried out by passing hydrogen chloride gas into the reaction mixture. The methyl ester can also be obtained by the action of diazomethane on the free acid.

Carboxylic acid derivatives of the general formula (I) where $R^3$ is COOH can be converted to a reactive acid derivative of the formula (IV)

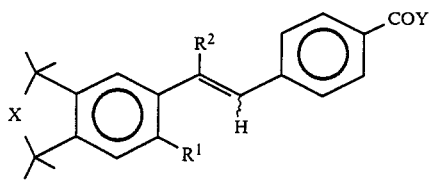

(IV)

where X, $R^1$ and $R^2$ have the above meanings and Y is a conventional reactive radical of a mixed anhydride or is halogen. These derivatives are advantageously reacted with an amine

or an alcohol $HOR^{13}$ in a solvent and in the presence or absence of an acid acceptor to give an amide or ester. In formula (IV), Y is halogen, in particular chlorine or bromine or, for example, the N-hydroxysuccinimide radical. These reactions of IV are carried out at as high as 50° C. under atmospheric pressure or in a closed vessel under superatmospheric pressure.

These reactions can be effected in the presence of a diluent or solvent, for example a lower saturated dialkyl ether, dialkylglycol ether or cyclic ether, such as diethyl ether, ethyl tert.-butyl ether, 1,2-dimethoxyethane, tetrahydrofuran or dioxane, an aromatic hydrocarbon, such as benzene, or an alkylbenzene, such as toluene or xylene, a saturated aliphatic hydrocarbon, such as hexane, heptane or isooctane, a lower aliphatic ketone, such as acetone, methyl ethyl ketone or methyl isobutyl ketone, a dialkylformamide, such as dimethylformamide or diethylformamide, or a mixture of the stated solvents. Linear or cyclic ethers, such as diethyl ether or tetrahydrofuran, and in particular dimethylformamide are preferably used, the reaction taking place in general at up to 30° C.

The reaction is usually carried out in the presence of a base as an acid acceptor. Suitable bases are alkali metal carbonates and bicarbonates, in particular those of sodium and potassium, tertiary organic bases, such as pyridine, and lower trialkylamines, such as trimethylamine or triethylamine. The base is used in a stoichiometric amount or in slight excess, based on the benzoyl halide employed.

Another possible method for the preparation of the compounds according to the invention starts from the corresponding acids of the formula IV where Y is OH; this is reacted with an amine

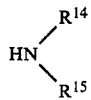

in a solvent in the presence of a carboxyl-activating agent which eliminates water.

Suitable activating reagents which eliminate water are the reagents conventionally employed in peptide synthesis, as described in, for example, The Peptides, Volume I, Academic Press, N.Y., 1965, pages 77 to 128. The general principle of the reaction consists in activating the carboxyl group, for example by treatment with a carbodiimide, such as N,N'-dicyclohexylcarbodiimide, or by forming, as an intermediate, the acid azide, a mixed anhydride (for example with monoesters of carbonic acid), an activated ester (for example the p-nitrophenyl ester) or a heterocyclic amide (for example an imidazolide) of the corresponding carboxylic acid (IV).

When a compound activated at the carboxyl group is treated with an amine

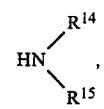

the compound according to the invention is obtained. The activation and coupling reactions can be carried out in solvents, preferably N,N-dimethylformamide, tetrahydrofuran, dioxane, methylene chloride, nitromethane, acetonitrile, dimethyl sulfoxide, N,N-dimethylacetamide or hexamethylphosphorotriamide. A suitable temperature for both stages, i.e. the reaction of the acid with the coupling agent and the reaction of the activated intermediate with the amine

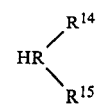

is from 20° to 100° C. A stepwise procedure, in which the activated intermediate is isolated before the addition of the amine, may be employed, but advantageously the reactants are reacted one after the other without isolation of intermediates. In a preferred coupling method, N,N-carbonyldiimidazole is used and the reaction is carried out in dimethylformamide, the reaction temperature for both stages being from 20° to 60° C.

Novel amides in which $R^{15}$ is hydrogen are preferably prepared by direct aminolysis of esters (containing the radical $-OR^{13}$) with a primary amine $H_2N-R^{15}$ at room temperature in the absence of a solvent or in the presence of an organic solvent, such as an alcohol, an ether, a dialkylformamide or a mixture of these.

An acyl halide of the formula (IV), preferably the acyl chloride, can be converted to an oxazoline derivative of the formula (I) by reaction with 2-aminoethanol or 2-amino-2-methylpropan-1-ol followed by cyclization.

A carboxylic acid, a carboxylate or a carboxamide of the formula (I) can be reduced to an alcohol or amine of the formula (I) in a conventional manner. Advantageously, the reduction is carried out with the aid of a metal hydride or alkali metal hydride in the presence of a suitable solvent. Preferably used metal hydrides are complex metal hydrides, such as lithium aluminum hydride or diisobutyl-aluminum hydride. Where lithium aluminum hydride is employed, the solvent used is an ether, such as diethyl ether, dioxane or tetrahydrofuran. If, however, the reduction is carried out using diisobutyl-aluminum hydride or an alkoxy-sodium aluminum hydride, a hydrocarbon, such as hexane or toluene, is preferably employed.

An amine or an alcohol of the formula (I) can be converted to the novel amide or ester of the formula (I) in a conventional manner using an alkanoyl halide or anhydride, an aralkyl halide or anhydride or an aroyl or hetaroyl halide or anhydride, advantageously in an inert diluent or solvent, for example a lower aliphatic ketone, such as acetone, methyl ethyl ketone or methyl isobutyl ketone, or a dialkylformamide, or by using excess acylating agent as the diluent or solvent. The reactions are preferably carried out in the presence of a base as an acid acceptor, at from −20° C. to the boiling point of the reaction mixture. Suitable bases are alkali metal carbonates, bicarbonates, hydroxides and alcoholates, in particular those of sodium and potassium, basic oxides, such as aluminum oxide or calcium oxide, tertiary organic bases, such as pyridine, and lower trialkylamines, such as trimethylamine or triethylamine. The bases can be used in a catalytic amount or in a stoichiometric amount or in slight excess, based on the alkylating agent employed.

An alcohol of the formula (I) can be reacted with an alkyl halide $R^{10}I$, $R^{10}Br$ or $R^{10}Cl$ in the presence of an alkali metal hydride, preferably sodium hydride, or in the presence of an alkyl-lithium compound, preferably n-butyllithium, in an organic solvent, such as tetrahydrofuran, dioxane, 1,2-dimethoxyethane, methyl tert.-butyl ether or, where sodium hydride is used, dimethylformamide, at from −10° to 40° C., to give an ether of the formula (I).

An alcohol of the formula (I) can be oxidized with a suitable oxidizing agent, preferably manganese(IV) oxide, if appropriate on an inorganic carrier, such as silica gel or alumina, to give an aldehyde of the formula (I). Advantageously, the reaction is carried out in an inert organic solvent, for example a hydrocarbon, such as hexane, an ether, e.g. tetrahydrofuran, or a mixture of the stated solvents and diluents, at from −10° to 30° C. The reaction time required depends substantially on the oxidation activity of the manganese(IV) oxide employed.

An aldehyde of the formula (I) may also be obtained by reduction of a nitrile of the formula (I) with diisobutyl-aluminum hydride in a solvent, preferably toluene, hexane, tetrahydrofuran or a mixture of these, at from −40° C. to room temperature.

The carbonyl compounds of the general formula (II) which are used as starting materials can be prepared in various ways, all of which are known in principle. Preferably, the parent substances of the general formula (V)

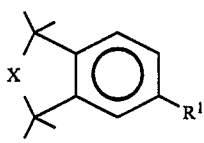

(V)

where X and $R^1$ have the stated meanings, are converted to the carbonyl compounds by a classical route, preferably by Friedel-Crafts reactions.

The novel compounds of the formula (I) may be obtained in the form of the pure cis or trans isomers or as a mixture of the E and Z isomers. Moreover, isomerization during the abovementioned reactions cannot be ruled out. The mixture of the novel compounds of the formula (I) resulting in such cases can be determined quantitatively by HPLC analysis or by means of a $^{13}C$-NMR spectrum, and the particular isomer desired can be isolated in pure form by fractional crystallization, by chromatography using, for example, a silica gel column, or by preparative HPLC.

Some of the compounds according to the invention possess an acidic hydrogen atom and can therefore be converted to a physiologically tolerated, readily water-soluble salt in a conventional manner using a base. Examples of suitable salts are ammonium salts, alkali metal salts, in particular those of sodium, of potassium and of lithium, alkaline earth metal salts, in particular those of calcium and of magnesium, and salts of suitable organic bases, such as lower alkylamines, e.g. methylamine or ethylamine, substituted lower alkylamines, in particular hydroxyl-substituted alkylamines, such as diethanolamine, triethanolamine or tris-(hydroxymethyl-)aminomethane, or piperidine or morpholine.

Amines of the formula (I) which are obtained according to the invention can be converted to their addition salts with physiologically tolerated acids by a conventional procedure. Examples of suitable conventional physiologically tolerated inorganic acids are hydrochloric acid, hydrobromic acid, phosphoric acid and sulfuric acid, and examples of organic acids are oxalic acid, maleic acid, fumaric acid, lactic acid, tartaric acid, malic acid, citric acid, salicylic acid, adipic acid and benzoic acid. Other examples are described in Fortschritte der Arzneimittelforschung, Volume 10, pages 224–225, Birkhäuser Verlag, Basel and Stuttgart, 1966.

Because of their pharmacological properties, the novel compounds and their physiologically tolerated salts can be used in the topical and systemic therapy and prophylaxis of precanceroses and carcinomas of the skin, the mucous membranes and internal organs, in the topical and systemic therapy of acne, psoriasis and other dermatological disorders accompanied by pathologically changed cornification, and for the treatment of rheumatic disorders, in particular those of an inflammatory or degenerative nature which affect the joints, muscles, tendons and other parts of the locomotor system. A preferred area of indication in addition to the therapy of dermatological disorders is the prophylactic and therapeutic treatment of precanceroses and tumors.

The pharmacological actions can be demonstrated, for example, in the following test models. In in vitro hamster tracheal tissue, the novel compounds eliminate the keratinization which sets in after vitamin A deficiency. This keratinization forms part of the early phase of carcinogenesis, which is inhibited in vivo by the novel compounds of the formula (I) using a similar technique after being induced by chemical compounds or high-energy radiation or after viral cell transformation. This method is described in Cancer Res. 36 (1976), 964–972, Nature 250 (1974), 64–66 and Nature 253 (1975), 47–50.

The compounds according to the invention also inhibit the proliferation rates of certain cells showing malignant changes. This method is described in J. Natl. Cancer Inst. 60 (1978), 1035–1041, Experimental Cell Research 117 (1978), 15–22 and Proc. Natl. Acad. Sci. USA 77 (1980), 2936–2940.

The antiarthritic action of the novel compounds can be determined in a conventional manner in animal experiments using the adjuvant arthritis model. The dermatological activity, for example in the treatment of acne, can be demonstrated by, inter alia, determining the comedolytic activity and the ability to reduce the number of cysts in the rhino mouse model.

This method is described by L. H. Kligman et al. in The Journal of Investigative Dermatology 73 (1979), 354–358, and J. A. Mezick et al. in Models of Dermatology (Ed. Maibach, Lowe), vol. 2, pages 59–63, Karger, Basel 1985.

The test substance in a suitable carrier was applied topically (100 μl) to the entire back area of the rhino mouse, application being affected once a day on five successive days per week for two weeks. About 72 hours after the final treatment, the dorsal skin was removed and left in 0.5% strength acetic acid for 18 hours at 4°–6° C. Thereafter, an area of about $2\times 5$ cm$^2$ was cut out and the epidermis was peeled off, placed on a microscope slide (with the dermal side upward) and washed water-free with alcohol/xylene until the epidermis appeared transparent. The sample was fixed by coating it with Permount, and evaluated microscopically. The diameters of 10 utricles in 5 freely selected areas were measured in each case, and the mean reduction in the utricle diameter was calculated from this by comparison with the untreated control group. The table below shows the results obtained.

TABLE

| Substance | Dose mg/ml | Reduction in the utricle diameter in % |
|---|---|---|
| Example 3 | 0.2 | 76.5 |
|  | 0.02 | 65.4 |
| Example 5 | 0.02 | 52.6 |
| Example 9 | 0.01 | 52.5 |

Accordingly, the present invention furthermore relates to therapeutic agents for topical and systemic administration which contain a compound of the formula (I) as an active compound, in addition to conventional carriers or diluents, and to the use of a compound of the formula (I) for the preparation of a drug.

The therapeutic agents or formulations are prepared in a conventional manner, for example by mixing an appropriate dose of the active compound with conventional solid or liquid carriers or diluents and conventional pharmaceutical auxiliaries, in accordance with the desired route of administration.

Accordingly, the agents can be administered perorally, parenterally or topically. Examples of formulations of this type are tablets, film tablets, coated tablets, capsules, pills, powders, solutions or suspensions, infusion or injectable solutions, and pastes, ointments, gels, creams, lotions, dusting powders, solutions or emulsions and sprays.

The therapeutic agents can contain the compounds used according to the invention in a concentration of from 0.0001 to 1%, preferably from 0.0001 to 0.1%, for local administration, and preferably in a single dose of from 0.1 to 50 mg for systemic administration, and can be administered daily in one or more doses, depending on the nature and severity of the illness.

Examples of conventional pharmaceutical auxiliaries are alcohols, such as isopropanol, oxyethylated castor oil or oxyethylated hydrogenated castor oil, polyacrylic acid, glycerol monostearate, liquid paraffin, vaseline, wool fat, polyethylene glycol 400, polyethylene glycol 400 stearate and oxyethylated fatty alcohols for local administration, and lactose, propylene glycol, ethanol, starch, talc and polyvinylpyrrolidone for systemic administration. If required, an antioxidant, for example tocopherol, butylated hydroxyanisole or butylated hydroxytoluene, or flavor-improving additives, stabilizers, emulsifiers, lubricants, etc. may be added to the preparations. All substances used in the preparation of pharmaceutical formulations must be toxicologically acceptable and compatible with the active compounds used.

The Examples which follow illustrate the invention.

A. PREPARATION OF THE STARTING MATERIALS

6-Acetyl-1,1,4,4-tetramethyl-2-tetralone and 6-acetyl-1,1,4,4-tetramethyl-3-tetralone 117.6 g of aluminum(III) chloride are added a little at a time to a solution of 47 ml of acetyl chloride in 200 ml of methylene chloride, and a solution of 80 g of 1,1,4,4-tetramethyl-2-tetralone in 120 ml of methylene chloride is added dropwise in the course of 1 hour. Stirring is then continued overnight at room temperature, and on the next day the mixture is poured onto 300 ml of ice water and extracted three times with methylene chloride. The organic phases are dried over sodium sulfate, the solution is evaporated down and the residue which remains is distilled. The fraction which boils at from 104° to 125° C. (0.2 bar) gives 80 g of a 1:1 mixture of the two title compounds.

B. PREPARATION OF THE COMPOUNDS ACCORDING TO THE INVENTION

EXAMPLE 1

Ethyl (E)-4-[2-(5,6,7,8-tetrahydro-5,5,8,8-tetramethyl-7-oxonaphth-2-yl)-1-propenyl]-benzoate A solution of 180 g of diethyl p-carboxyethylbenzylphosphonate in 120 ml of dimethyl sulfoxide is added dropwise, in the course of 1 hour at about 35° C., to a suspension of 18 g of 80% strength sodium hydride in 480 ml of dimethyl sulfoxide, the sodium hydride having been freed beforehand from the 20% of paraffin with petroleum ether. The mixture is then stirred for a further 45 minutes at room temperature, and a solution of 73.2 g of the mixture of ketones, i.e. 6-acetyl-1,1,4,4-tetramethyl-2-tetralone and -3-tetralone, in 180 ml of tetrahydrofuran is added dropwise in the course of 25 minutes.

Next day, the mixture is poured on to 2 l of ice water and acidified with dilute hydrochloric acid. The resulting solid (which contains a mixture of ethyl 6-oxo- and 7-oxobenzoate) is filtered off, and the residue is washed on the filter with water and ethanol and recrystallized from ethyl acetate. The crystals are taken up in 160 ml of methylene chloride, 1.6 liters of n-heptane are added, and the precipitate which forms is filtered off and dried to give 27.1 g of the title compound of melting point 173°–174° C.

EXAMPLE 2

(E)-4-[2-(5,6,7,8-Tetrahydro-5,5,8,8-tetramethyl-7-oxo-naphth-2-yl)-1-propenyl]-benzoic acid 2 g of ethyl (E)-4-[2-(5,6,7,8-tetrahydro-5,5,8,8-tetramethyl-7-oxonaphth-2-yl)-1-propenyl]-benzoate are stirred with 0.7 g of potassium hydroxide in a mixture of 25 ml of ethanol and 1.5 ml of water for 3 hours at 80° C. The entire reaction mass is introduced into 100 ml of water, after which the mixture is acidified with 2 N hydrochloric acid, and the resulting precipitate is filtered off, washed with cold methanol and dried to give 1.3 g of the title compound of melting point 260°–261° C.

EXAMPLE 3

(E)-4-[2-(5,6,7,8-Tetrahydro-5,5,8,8-tetramethyl-7-hydroxynaphth-2-yl)-1-propenyl]-benzyl alcohol A solution of 8.8 g of ethyl (E)-4-[2-(5,6,7,8-tetrahydro-5,5,8,8-tetramethyl-7-oxonaphth-2-yl)-penyl]-benzoate in 200 ml of tetrahydrofuran is added dropwise to a stirred suspension of 1 g of lithium aluminum hydride in 330 ml of diethyl ether. The mixture is refluxed for 4 hours, after which a saturated tartaric acid solution is added dropwise and the mixture is extracted several times with diethyl ether. The combined organic phases are washed neutral, dried over sodium sulfate and freed from the solvent. The remaining solid residue is dissolved in 10 ml of tetrahydrofuran and 100 ml of methanol at about 80° C., and 400 ml of water are added. The resulting crystals are filtered off and dried to give 4.7 g of the title compound of melting point 184°–185° C.

EXAMPLE 4

(a)

(E)-4-[2-(5,6,7,8-Tetrahydro-5,5,8,8-tetramethyl-6-oxonaphth-2-yl)-1-propenyl]-benzonitrile A solution of 56 g of diethyl p-cyanobenzylphosphonate in 115 ml of dimethyl sulfoxide is added dropwise, in the course of 1 hour at about 40° C., to a suspension of 7 g of 80% strength sodium hydride in 230 ml of dimethyl sulfoxide, the sodium hydride having been freed beforehand from the 20% of paraffin with petroleum ether. The mixture is then stirred for a further 30 minutes at room temperature, and 38 g of the ketone mixture, i.e. 6-acetyl-1,1,4,4-tetramethyl-3-tetralone and 6-acetyl-1,1,4,4-tetramethyl-3-tetralone an 6-acetyl-1,1,4,4,-tetramethyl-2-tetralone, in 50 ml of dimethyl sulfoxide and 150 ml of tetrahydrofuran are added dropwise in the course of 10 minutes. After 3 hours, the mixture is poured on to ice water and acidified with dilute hydrochloric acid, and the resulting solid is filtered off and washed on the filter with methanol and ethyl acetate in succession.

The solid is then dissolved in 350 ml of acetone and 350 ml of tetrahydrofuran, and 350 ml of water are slowly added to this solution. The resulting crystals are filtered off under suction, washed with methanol and dried to give 25 g of a mixture of 7 parts of the 7-oxo compound and 3 parts of the title compound. The structure was assigned on the basis of an NO experiment. 3.3 g of the title compound of melting point 170°–171° C. crystallize from the mother liquor after it has stood for one day.

(b)

(E)-4-[2-(5,6,7,8-Tetrahydro-5,5,8,8-tetramethyl-7-oxonaphth-2-yl)-1-propenyl]benzonitrile 15.1 g of the title compound of melting point 222°–223° C. are obtained from 25 g of the mixture, described above, of 7 parts of 7-oxobenzonitrile and 3 parts of 6-oxobenzonitrile by recrystallizing repeatedly from ethyl acetate.

EXAMPLE 5

(E)-4-[2-(5,6,7,8-Tetrahydro-5,5,8,8-tetramethyl-6-oxonaphth-2-yl)-1-propenyl]-benzoic acid Using procedures similar to that described in Example 2, 2.5 g of the title compound of melting point 249°–250° C. are obtained from 2.1 g of (E)-4-[2-(5,6,7,8-tetrahydro-5,5,8,8-tetramethyl-6-oxonaphth-2-yl)-1-propenyl]-benzonitrile and 30 ml of 10 N sodium hydroxide solution in 30 ml of propan-2-ol after a reaction time of 7 hours.

EXAMPLE 6

(E)-4-[2-(5,6,7,8-Tetrahydro-5,5,8,8-tetramethyl-7-hydroxynaphth-2-yl)-1-propenyl]-benzaldehy 50 ml of a 1.2 molar solution of diisobutylaluminum hydride in toluene are added to a stirred suspension of 5.1 g of (E)-4-[2-(5,6,7,8-tetrahydro-5,5,8,87-oxonaphth-2-yl)-1-propenyl]-benzonitrile. After 2 hours at room temperature, a saturated tartaric acid solution is added, and the mixture is extracted several times with ether. The combined organic phases are washed neutral with water, dried over sodium sulfate and freed from the solvent. The crude residue which remains is subjected to flash chromatography over silica gel to give 3.2 g of the title compound in amorphous form. The material can, if desired, be further processed directly in this form.

EXAMPLE 7

(E)-4-[2-(5,6,7,8-Tetrahydro-5,5,8,8-tetramethyl-7-hydroxynaphth-2-yl)-1-propenyl]-benzyl alcohol 3.2 g of the aldehyde from Example 6 is reduced with sodium borohydride in isopropanol as described in Example 3. 1.3 g of the title compound of melting point 182°–183° C. are obtained.

EXAMPLE 8

(E)-4-[2-(5,6,7,8-Tetrahydro-5,5,8,8-tetramethyl-7-hydroxynaphth-2-yl)-1-propenyl]-benzonitrile 2.2 g (6.5 mmol) of the ketonitrile of Example 4b are added at reflux temperature to a mixture of 6.1 g (30 mmol) of aluminum isopropylate, 60 ml of absolute isopropanol and 30 ml of toluene. About 100 ml of solvent mixture are distilled off in the course of 8 hours and replaced with the same amount of a 9:1 mixture of isopropanol and toluene. This procedure is repeated until acetone can no longer be detected in the distillate (dinitrophenylhydrazine test). The mixture is allowed to cool and evaporated to dryness, and 20 g of ice and 20 ml of 2 N HCl are added. The mixture is stirred vigorously, the solid is filtered off under suction, the residue is washed with 5 ml of methanol and dried to give 2.1 g of the title compound of melting point 163°–165° C.

EXAMPLE 9

(E)-4-[2-(5,6,7,8-Tetrahydro-5,5,8,8-tetramethyl-7-hydroxynaphth-2-yl)-1-propenyl]-benzoic acid Similarly to the method described in Example 2, 1.5 g of the title compound of melting point 250°–252° C. are obtained after a reaction time of about 5 hours from 2.1 g of (E)-4-[2-(5,6,7,8-tetrahydro-5,5,8,8-tetramethyl-7-hydroxy-naphth-2-yl)-1-propenyl]-benzonitrile (Example 8) and 42 ml of 10 N sodium hydroxide solution in 42 ml of ethanol.

EXAMPLE 10

(E)-4-[2-(5,6,7,8-Tetrahydro-5,5,8,8-tetramethyl-7-oxonaphth-2-yl-1-propenyl]-benzoic acid azide A solution of 6 ml of triethylamine in 30 ml of acetone is allowed to run into a suspension of 12.7 g (35 mmol) of (E)-4-[2-(5,6,7,8-tetrahydro-5,5,8,8-tetramethyl-7- oxo-naphth-2-yl)-1-propenyl]-benzoic acid (Example 2) in 60 ml of acetone and 20 ml of water, at 0°–5° C. At 0° C. 4.5 ml (5.2 g, 55 mmol) of ethyl chloroformate are added dropwise, the solution is stirred for a further 10 minutes and a solution of 3.5 g (55 mmol) of sodium azide in 7.5 ml of water is then added dropwise. The solution is stirred at 0° C. for a further 2 hours, the finely crystalline solid is filtered off under suction and the residue is washed with a little water and ethanol and dried, to give 10.8 g of the title compound which is processed further without purification (see Example 11).

EXAMPLE 11

(E)-4-[2-(5,6,7,8-Tetrahydro-5,5,8,8-tetramethyl-7-oxo-naphth-2-yl)-1-propenyl]benz(2-hydroxyethyl)amide 10 ml of ethanolamine are added to a solution of 1.9 g (5 mmol) of the acid azide of Example 10 in 100 ml of tetrahydrofuran, the mixture is stirred briefly and allowed to stand for 20 minutes at room temperature. The clear solution is poured onto 400 ml of water, acidified and the resulting precipitate is filtered off under suction. The residue is washed with 5 ml of methanol, dried and recrystallized from ethyl acetate/toluene (3:1) to give 1.1 g of the title compound of melting point 201°–203° C.

EXAMPLE 12

(E)-4-[2-(5,6,7,8-Tetrahydro-5,5,8,8-tetramethyl-7-oxo-naphth-2-yl)-1-propenyl]benz(n-butyl)amide 1.4 ml (1.6 g, 15 mmol) of ethyl chloroformate in 10 ml of acetone are added dropwise to a mixture of 3.6 g (10 mmol) of (E)-4-[2-(5,6,7,8-tetrahydro-5,5,8,8-tetramethyl- 7-oxo-naphth-2-yl)-1-propenyl]-benzoic acid (Example 2), 1.8 ml (12.5 mmol) of triethylamine and 40 ml of acetone at 0° C. The solution is stirred at this temperature for 30 minutes, and a solution of 1.5 g (20 mmol) of n-butylamine in 20 ml of acetone is then added dropwise at 0° C. The solution is allowed to reach room temperature, diluted with 30 ml of acetone, a further 3 g (40 mmol) of n-butylamine are added after 2 hours and the mixture is stirred overnight.

The mixture is poured onto 400 ml of water acidified with 2N HCl and the resulting solid is filtered off under suction, washed with water and methanol and dried. The resulting crude product (3.6 g) is recrystallized from 200 ml of methanol and then subjected to flash chromatography (200 g Si 60; n-heptane with increasing amounts of ethyl acetate). 1 g of the title compound of melting point 112°–174° C. are thus obtained.

EXAMPLE 13

(E)-4-[2-(5,8-Dihydro-5,5,8,8-tetramethyl-naphth-2-yl)-1-propenyl]-benzonitrile 5 g (14.5 mmol) of ketonitrile from Example 4 (7-oxo : 6-oxo =9:1), 3.5 g (18.7 mmol) of p-toluenesulfonic acid hydrazide (96% strength) and about 200 mg of p-toluenesulfonic acid are refluxed in 50 ml of dimethoxyethane for 4 hours. The solvent is then removed in a rotary evaporator and the residue is taken up in 50 ml of diethylene glycol dimethyl ether. 1 g (18.5 mmol) of solid sodium methylate are added, the mixture is stirred at room temperature for 15 minutes and then heated slowly to the reflux temperature ( ~140° C.). After 1 hour at 140° C., evolution of nitrogen is complete. The mixture is cooled, extracted with ether/water, the ether phase is washed thoroughly several times with water, dried over $Na_2SO_4$ and evaporated down. The crude product is successively purified by recrystallization from methanol/chloroform, flash chromatography (Si 60; $CH_2Cl_2$) and once again recrystallization from methanol/chloroform. 1.1 g of the title compound of melting point 140°–142° C. are thus obtained.

EXAMPLE 14

(E)-4-[2-(5,8-Dihydro-5,5,8,8-tetramethyl-naphth-2-yl)-1-propenyl]-benzoic acid

Similarly to the method described in Example 2, 0.9 g of the title compound of melting point 234°–236° C. is obtained after a reaction time of about 5 hours from 1 g (2.6 mmol) of (E)-4-[2-(5,8-dihydro-5,5,8,8-tetramethyl-naphth-2-yl)-1-propenyl]-benzonitrile (Example 13) and 15 ml of 10 N sodium hydroxide solution in 15 ml of ethanol.

We claim:

1. A tetralin derivative of the formula I

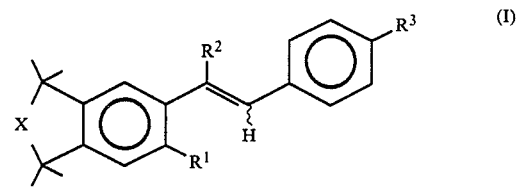

where $R^1$ is hydrogen, $C_1$–$C_4$-alkyl, $C_1$–$C_4$-alkoxy or halogen $R^2$ is hyorogen, $C_1$–$C_6$-alkyl or $C_3$–$C_6$-cycloalkyl, X is —$CH_2$—CO—, —$CH_2$—CHOH, —$CH_2$—C($R^4$)OH—, —$CH_2$—C(OCOR_4)H—, —$CH_2$—C($R^4$)(OCHOR$^5$)—, —CHOH—CHOH—, —CH(OCOR$^4$)—CH(OCOR_4)—, —$CH_2$—CH(OR$^4$)— or

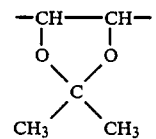

(where $R^4$ and $R^5$ are each $C_1$–$C_4$-alkyl) and $R^3$ is nitrile, $C_2$ $C_{10}$-ketal or —CH($R^7$)($R^8$)— or —CO—$R^9$, where $R^7$ is hydrogen or $C_1$–$C_3$-alkyl, $R^8$ is hydrogen, $C_1$–$C_3$-alkyl or —$OR^{10}$ or —$NR^{11}R^{12}$ (where $R^{10}$, $R^{11}$ and $R^{12}$ are each hydrogen, $C_1$–$C_4$-alkyl, $C_2$–$C_{20}$-alkanoyl or unsubstituted or substituted benzoyl, or $R^{11}$ and $R^{12}$, together with the nitrogen atom to which they are bonded, form a heterocyclic radical) and $R^9$ is hydrogen, halogen, $C_1$–$C_4$-alkyl, azido, imidazolyl, triazolyl or —$OR^{13}$ or —$NR^{14}R^{15}$ (where $R^{13}$ is hydrogen or $C_1$–$C_8$-alkyl or is $C_2$–$C_6$-alkyl which is substituted by one or more hydroxyl groups or a $C_1$–$C_4$-alkoxy group, or is unsubstituted or substituted aryl or aralkyl which is unsubstituted or substituted in the aryl moiety, and $R^{14}$ and $R^{15}$ are each hydrogen or $C_1$–$C_6$-alkyl or are each $C_2$–$C_6$-alkyl which is substituted by one or more hydroxyl groups or are each aryl or tetrazolyl, or $R^{14}$ and $R^{15}$, together with the nitrogen atom to which they are bonded, for a heterocyclic ring system possessing 3 to 6 ring atoms), and, where relevant, its physiologically tolerated salts.

2. A tetralin derivative of the formula I as set forth in claim 1, which is present in the E form.

3. A tetralin derivative of the formula I as set forth in claim 1 wherein X is —$CH_2$—CO—, —$CH_2$—CHOH—, —CHOH—CHOH or —CH=CH, $R^1$ is hydrogen, methyl, methoxy or fluorine, $R^2$ is hydrogen or methyl, and $R^3$ is —COOH, —COO—$C_1$-$C_4$-alkyl, —CHO, —$CH_2$OH or —$CH_2$—O—CO—$CH_3$.

4. A tetralin derivative as set forth in claim 1, which is (E)-4-[2-(5,6,7,8-tetrahydro-5,5,8,8-tetramethyl-7-hydroxynaphth-2-yl)-1-propenyl]-benzyl alcohol.

5. A tetralin derivative as set forth in claim 1, which is (E)-4-[2-(5,6,7,8-tetrahydro-5,5,8,8-tetramethyl-6-oxo-naphth-2-yl)-1-propenyl]-benzoic acid.

6. A tetralin derivative as set forth in claim 1, which is (E)-4-[2-(5,6,7,8-tetrahydro-5,5,8,8-tetramethyl-7-hydroxynaphth-2-yl)-1-propenyl]-benzoic acid.

7. A tetralin derivatives as set forth in claim 1, which is (E)-4-[2-(5,8-dihydro-5,5,8,8-tetramethyl-naphth-2-yl)-1-propenyl]-benzoic acid.

8. A therapeutic composition for treating dermatological disorders comprising a pharmaceutically acceptable carrier and an effective amount of a tetralin derivative as defined in claim 1 as the active agent.

9. The method of treating dermatological disorders in a patient suffering therefrom which comprises administering to the patient an effective amount of a tetralin derivative as defined in claim 1 as the active agent.

10. The composition of claim 8, wherein the active agent is the tetralin derivative of claim 4.

11. The composition of claim 8, wherein the active agent is the tetralin derivative of claim 5.

12. The composition of claim 8, wherein the active agent is the tetralin derivative of claim 6.

13. The composition of claim 8, wherein the active agent is the tetralin derivative of claim 7.

14. The method of claim 9, wherein the active agent is the tetralin derivative of claim 4.

15. The method of claim 9, wherein the active agent is the tetralin derivative of claim 5.

16. The method of claim 9, wherein the active agent is the tetralin derivative of claim 6.

17. The method of claim 9, wherein the active agent is the tetralin derivative of claim 7.

* * * * *